United States Patent [19]

Seto et al.

[11] Patent Number: 4,576,934
[45] Date of Patent: Mar. 18, 1986

[54] ANTIHYPERTENSIVE DIHYDROPYRIDINE-5-PHOSPHONIC ACID CYCLIC ESTERS

[75] Inventors: Kiyotomo Seto, Funabashi; Sakuya Tanaka, Hasuda; Ryozo Sakoda, Kashiwa, all of Japan

[73] Assignee: Nissan Chemical Industries Ltd., Tokyo, Japan

[21] Appl. No.: 654,473

[22] Filed: Sep. 26, 1984

[30] Foreign Application Priority Data

Sep. 26, 1983 [JP] Japan ............................... 58-177710
Aug. 3, 1984 [JP] Japan ............................... 59-163649

[51] Int. Cl.⁴ ...................... C07F 9/58; A61K 31/675
[52] U.S. Cl. ................................... 514/85; 514/89; 546/21; 544/337
[58] Field of Search ........................ 546/21; 424/200; 544/337; 514/85, 89

[56] References Cited

U.S. PATENT DOCUMENTS 3,485,847 12/1969 Bossert ............................. 546/321
4,393,070 7/1983 Sato et al. ....................... 546/321
4,532,248 7/1985 Franckowiak et al. ............ 514/302
4,535,073 8/1985 Kimura et al. ..................... 546/21

FOREIGN PATENT DOCUMENTS 0071819 2/1983 European Pat. Off. .
0121117 10/1984 European Pat. Off. .
2105989 4/1983 United Kingdom .

Primary Examiner—Henry R. Jiles
Assistant Examiner—Dale A. Bjorkman
Attorney, Agent, or Firm—Oblon, Fisher, Spivak, McClelland & Maier

[57] ABSTRACT

A compound of the formula:

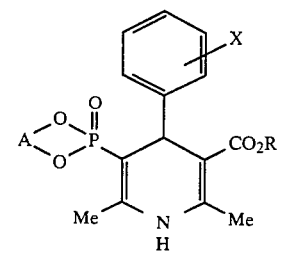

where X is hydrogen, nitro, trifluoromethyl, fluorine, chlorine, bromine or iodine; A is 1,3-propylene or 1,4-butylene which may be substituted by $C_1$–$C_3$ alkyl, R is $C_1$–$C_4$ alkyl, —Y—N($R^1$)($R^2$) or

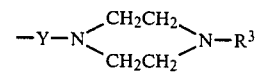

where each of $R^1$, $R^2$ and $R^3$, which may be the same or different are hydrogen, $C_1$–$C_6$ alkyl, or aralkyl, and Y is $C_2$–$C_6$ alkylene, and Me is methyl, or its pharmaceutically acceptable salt. These compounds have utility as anti-hypertensive agents and coronary or peripheral vasodilators.

9 Claims, No Drawings

ANTIHYPERTENSIVE DIHYDROPYRIDINE-5-PHOSPHONIC ACID CYCLIC ESTERS

BACKGROUND OF THE INVENTION

1. Field of the Invention

The present invention relates to a novel 1,4-dihydropyridine-5-phosphonic acid cyclic ester, a process for the preparation thereof, and an antihypertensive agent or coronary or peripheral vasodilator composition containing the novel ester or its pharmaceutically acceptable salt.

2. Description of the Prior Art 1,4-Dihydropyridines are known to be useful for the medical treatment of coronary heart diseases, cerebral diseases, hypertension or arrhythmia, as they are capable of inhibiting the contraction of smooth muscle and cardiac muscle by calcium antagonistic effects (see A. Fleckenstein, Annu. Rev. Pharmacol. Toxicol., 17, 149–166 (1977)). However, the majority of 1,4-dihydropyridines known or being developed are substituted at the 3- and 5-positions by a carboxylic acid ester group.

Dihydropyridine-5-phosphonate derivatives are disclosed in prior art references. However, none of these references suggests or indicates the specific compounds of the present invention.

Relevant references are as follows: A. I. Razumov et al. synthesized a dihydropyridine-4-alkyl-5-phosphonate derivative (Zh. Obshch. Khim., 47, 1190–1191 (1977) and ibid., 51, 547–552 (1981)). Further, Von K. Issleib et al. synthesized 1,4-dihydropyridine-4-aryl-5-phosphonates (more specifically, diethyl 2,6-dimethyl-4-phenyl-3-ethoxy carbonyl-1,4-dihydropyridine-5-phosphonate and diethyl 2,6-dimethyl-4-(4-methoxyphenyl)-3-ethoxy carbonyl-1,4-dihydropyridine-5-phosphonate) (J. Prakt. Chem., Vol. 318, 207–220 (1976)). None of these references indicates the pharmacological activities. Furthermore, U.K. Patent Application GB No. 2105989A discloses a wide range of 1,4-dihydropyridine-5-phosphonate derivatives by a general formula, and teaches that the compounds represented by the general formula have cardiac activities. However, the specification of this Patent Application discloses no actual examples for the syntheses of 1,4-dihydropyridine-5-phosphonate derivatives and no pharmacological data relating to such derivatives.

SUMMARY OF THE INVENTION

The present invention provides novel compounds represented by the formula:

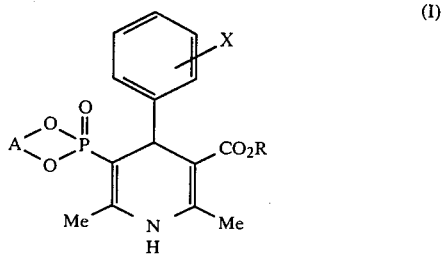

(I)

where X is a hydrogen atom, a nitro group, a trifluoromethyl group, a fluorine atom, a chlorine atom, a bromine atom or an iodine atom, A is a 1,3-propylene or 1,4-butylene group which is unsubstituted or substituted by an alkyl group having 1 to 3 carbon atoms, R is an alkyl group having 1 to 4 carbon atoms, $-Y-N(R^1)(R^2)$ or

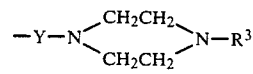

where each of $R^1$, $R^2$ and $R^3$, which may be the same or different, is a hydrogen atom, an alkyl group having 1 to 6 carbon atoms or an aralkyl group, and Y is an alkylene group having 2 to 6 carbon atoms, and Me is a methyl group, or its pharmaceutically acceptable salt.

Some of the compounds of the formula I have optical isomers or diastereomers. The present invention covers such optical isomers and diastereomers.

The present invention also provides antihypertensive agents or coronary or peripheral vasodilator compositions comprising an effective amount of the compounds of formula I or its pharmaceutically acceptable salts, and a pharmaceutically acceptable diluent or carrier.

Further, the present invention provides a process for producing the compound of the formula I, which comprises reacting a compound of the formula II with a compound of the formula III, as shown by Scheme 4 given hereinafter.

DESCRIPTION OF THE PREFERRED EMBODIMENTS

The compounds of the present invention can be prepared in accordance with the flow chart of the following Scheme 1.

Scheme 1

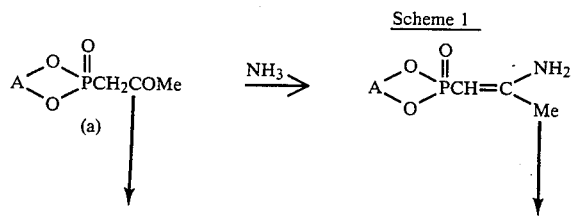

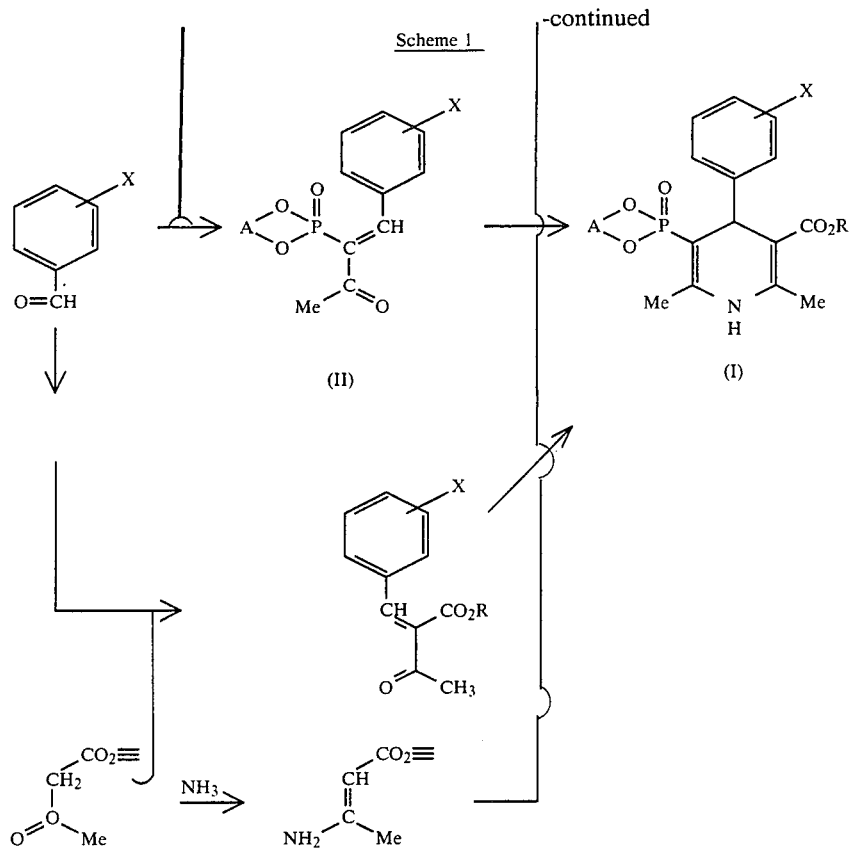

Scheme 1

(II)  (I)

In Scheme 1, A, R, Me and X have the same meanings as defined with respect to the general formula I.

The acetonyl phosphonic acid cyclic ester (a) i.e. one of the starting compounds, is a novel compound. This compound can be prepared by means of a conventional technique (see D. W. White, J. Am. Chem. Soc., 92, 7125–7135 (1970)). Namely, as shown by Scheme 2, it is obtainable by the reaction of a 1-methoxy-1-phosphorus-2,6-dioxacyclohexane derivative (a-2) or a 1-methoxy-1-phosphorus-2,7-dioxacycloheptane derivative (a-2) with iodoacetone.

Scheme 2

(a-2)  (a)

In Scheme 2, A and Me have the same meanings as defined with respect to the general formula I.

As specific examples of —A—, there may be mentioned the following groups:

—(CH$_2$)$_2$CH(Me)—, —CH(Me)CH$_2$CH(Me)—, —CH$_2$C(Me)$_2$CH$_2$—,

—CH(Me)CH$_2$CH$_2$CH(Me)—, —CH(Me)CH(Me)CH(Me)—,

—CH$_2$C(Et)$_2$CH$_2$—, —CH$_2$CH(Et)CH(n—C$_3$H$_7$)— and

—CH$_2$C(Et)(n—C$_4$H$_9$)CH$_2$—, where Me is a methyl group, and Et is an ethyl group.

The compounds of the present invention may also be obtained by preparing a 1,4-dihydropyridine-5-phosphonic acid monoester (a-3), followed by the cyclization of the ester portion, in accordance with Scheme 3.

Scheme 3

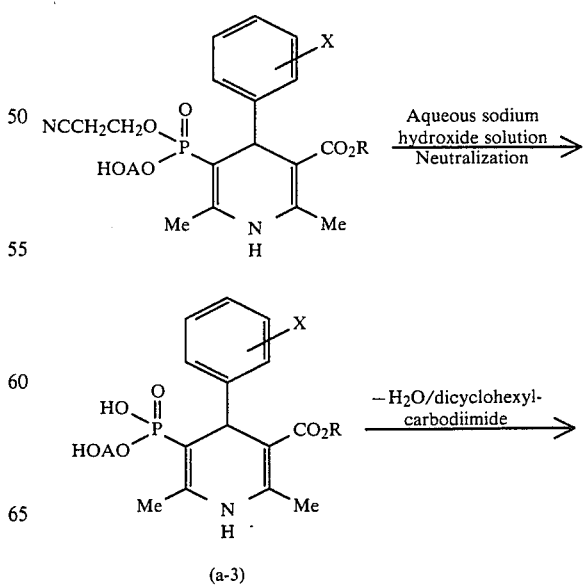

(a-3)

-continued
Scheme 3

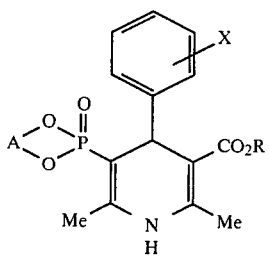

In Scheme 3, A, X, Me and R have the same meanings as defined with respect to the general formula I.

Among the reactions shown in Scheme 1, the reaction of the following Scheme 4 will be described in further detail.

Scheme 4

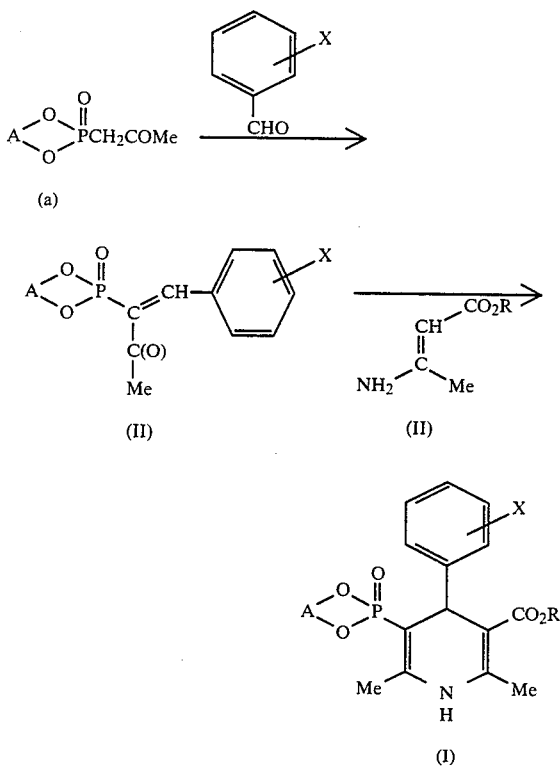

In Scheme 4, A, X, Me and R have the same meanings as defined with respect to the general formula I.

The present invention also provides a process for producing the compound of the formula I by reacting the compound of the formula II with the compound of the formula III in an inert solvent in accordance with the above Scheme 4. The starting compound of the formula II is obtainable by reacting the acetonyl phosphonic acid cyclic ester (a) with a benzaldehyde by means of a conventional technique. Likewise, the starting compound of the formula III can readily be obtained by reacting the corresponding carbonyl compound with ammonia. The starting compound of the formula III may be formed in the reaction system simply by mixing the corresponding carbonyl compound with ammonia and is not necessarily required to be isolated.

The inert solvent includes an alcohol solvent such as methanol, ethanol, propanol or isopropanol, an ether solvent such as 1,2-dimethoxyethane or THF, an aromatic hydrocarbon solvent such as benzene, toluene or xylene, a nitrile solvent such as acetonitrile or benzonitrile, an amido solvent such as DAM, DMF or N-methylpyrrolidone, a sulfoxide solvent such as DMSO or sulfolane, an ester solvent such as ethyl acetate or butyrolactone, or pyridine.

The reaction is usually conducted at a temperature of from room temperature to 200° C., preferably from 60° to 140° C., for from 1 to 100 hours, preferably from 5 to 20 hours.

As mentioned above, the compounds of the present invention are not only capable of inhibiting the contraction of smooth muscle and cardiac muscle by the calcium antagonistic effects but also antihypertensively effective when administered orally. Thus, they are useful for the medical treatment of the coronary heart diseases, cerebral diseases or hypertension of mammals.

Thus, the present invention provides an antihypertensive agent or coronary or peripheral vasodilator composition comprising an effective amount of the compound of the formula I or its phamaceutically acceptable salt, and a phamarceutically acceptable diluent or carrier. Such a composition may also be formulated into a veterinary composition by combining the compound of the present invention with a veterinarily acceptable diluent or carrier.

Such compositions may be used in the form suitable for oral administration, e.g. tablets or capsules, in the form suitable for transdermal administration, e.g. ointments or plasters, in the form suitable for inhalation, e.g. aerosols or solutions suitable for spraying, in the form suitable for injection administration, e.g. a sterilized aqueous solution, or in the form of a suppository suitable for use in anus, vagina or rectum.

The compositions of the present invention usually contain the compound of the formula I in an amount of from about 0.1 to about 99.5% by weight, preferably from about 0.5 to about 95% by weight, based on the total weight of the composition.

The compounds of the present invention or the compositions of the present invention may be used in combination with other pharmaceutically or veterinarily active compounds. Further, the composition of the present invention may contain a plurality of the compounds of the formula I.

The daily dose of the compounds of the formula I may be varied depending upon the type and the condition of the disease to be cured and the type of the patient (the age, sex, sensitivity, etc.). In the case of the intravenous administration, the daily dose is usually from 0.0001 to 10 mg, preferably from 0.0005 to 1 mg, of the active ingredient per 1 kg of the body weight. Likewise, in the case of the oral or transdermal administration, the daily dose is usually from 0.001 to 100 mg of the active ingredient per 1 kg of the body weight. Further, the daily dose in the case of the administration in the form of a suppository to e.g. a vagina or rectum, is usually from 0.001 to 200 mg, preferably from 0.005 to 100 mg, of the active ingredient per 1 kg of the body weight. The content of the active ingredient in an aerosol, is usually from 0.1 to 10% by weight, preferably from 0.1 to 2% by weight. Such a daily dose may be divided for administration twice or more times per day.

The above-mentioned compositions containing the compounds of the formula I may be prepared by a conventional method, and a conventional excipient may be incorporated therein.

Referring to the formula I, it is preferred that A is a 1,3-propylene or 1,4-butylene group which is unsubstituted or substituted by one or two methyl groups, such as

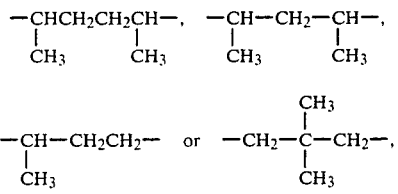

R is

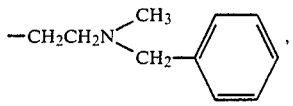

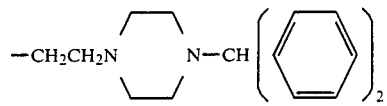

or an alkyl group having 1 to 4 carbon atoms, particularly CH₃, more preferably

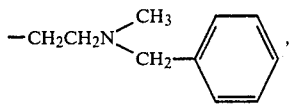

and X is NO₂, CF₃, F, Cl, Br or I substituted at the 2- or 3-position, more preferably CF₃, NO₂ or Cl substituted at the 2- or 3-position.

The present invention will now be described in further detail with reference to Working Examples, Test Examples and various formulations. However, it should be understood that the present invention is by no means restricted by these specific Examples. In the following Examples, Me represents a methyl group, and Et represents an ethyl group.

EXAMPLES

EXAMPLE 1

Synthesis of β-(N-benzyl-N-methylamino)-ethyl 5-(3,6-dimethyl-1-oxo-1-phospha-2,7-dioxacycloheptyl)-2,6-dimethyl-1,4-dihydro-4-(3-nitrophenyl)pyridine-3-carboxylate 0.45 g of β-(N-benzyl-N-methylamino)-ethyl-3-aminocrotonate and 0.53 g of 1-(α-acetyl-3-nitrostyryl)-3,6-dimethyl-1-oxo-1-phospha-2,7-dioxacycloheptane were dissolved in 20 ml of toluene, and the solution was refluxed for 15 hours. Then, the solvent was distilled off under reduced pressure, and the residue was subjected to silica gel column chromatography by using 10% ethanol-ethyl acetate as the developer. The fraction containing the desired substance was distilled under reduced pressure to remove the solvent, whereby the above-identified compound was obtained.

In a similar manner, compounds of Examples 2 to 22 were obtained. The characteristics of the compounds thus obtained are shown in Table 1, and their spectral data are shown in Table 2.

TABLE 1

Compounds of Examples 1 to 22 and their characteristics

| Example Nos. | X | Yield | Characteristics |
|---|---|---|---|
| 1 | 3-NO₂ | 57% | Yellow oily substance |
| 2 | 2-CF₃ | 61% | Yellow oily substance |
| 3 | 3-Cl | 73% | Yellow oily substance |
| 4 | 2-Cl | 81% | Yellow oily substance |
| 5 | 3-NO₂ | 73% | Yellow semisolid |
| 6 | 2-CF₃ | 61% | Yellow semisolid |
| 7 | 3-Cl | 64% | Light yellow crystals (mp 136–139° C.) |
| 8 | 2-Cl | 67% | Yellow semisolid |
| 9 | 3-NO₂ | 66% | Yellow semisolid |
| 10 | 2-CF₃ | 62% | Yellow semisolid |
| 11 | 2-Cl | 69% | Yellow semisolid |
| 12 | 3-NO₂ | 64% | Yellow semisolid |
| 13 | 2-CF₃ | 77% | Yellow semisolid |
| 14 | 3-Cl | 77% | Yellow crystals (mp 138.5–139° C.) |
| 15 | 2-Cl | 83% | Yellow oily substance |

TABLE 1-continued
Compounds of Examples 1 to 22 and their characteristics

[Structure: dimethyl-substituted dioxaphosphorinane attached to dihydropyridine with phenyl-X group and CO₂CH₂CH₂N(Me)CH₂Ph ester]

| Example Nos. | X | Yield | Characteristics |
|---|---|---|---|
| 16 | m-NO₂ | 60% | Yellow semisolid |
| 17 | o-CF₃ | 59% | Yellow semisolid |
| 18 | m-Cl | 79% | Yellow semisolid |
| 19 | o-Cl | 69% | Yellow semisolid |

[Structure: cyclic phosphonate A-O-P(=O)-O- attached to dihydropyridine with o-CF₃ phenyl and CO₂Me]

| Example Nos. | A | Yield | Characteristics |
|---|---|---|---|
| 20 | —CH(Me)CH₂CH₂— | 24% | Yellow oily substance |
| 21 | —CH(Me)CH₂CH(Me)— | 70% | Yellow semisolid |
| 22 | —CH₂C(Me)₂CH₂— | 27% | Colorless crystals (mp 211–214° C.) |

TABLE 2
Compounds of Examples 1 to 22 and their spectral data

| Example Nos. | NMR spectrum δ-value (in CDCl₃) | Mass spectrum m/e (intensity ratio) |
|---|---|---|
| 1 | 8.20–7.10(4H, m), 7.25(5H, s), 4.88(1H, d, J=10Hz), 4.90–4.00(2H, m), 4.17(2H, t, J=6Hz), 3.50(2H, s), 2.65(2H, t, J=6Hz), 2.40–2.10(9H, m), 2.07–0.90(10H, m) | 134(100), 314(8), 419(10), 566(18), 583(4, M⁺) |
| 2 | 7.75–7.00(4H, m), 7.25(5H, s), 5.38(1H, d, J=10Hz), 4.85–3.90(2H, m), 4.17(2H, t, J=6Hz), 3.50(2H, s), 2.65(2H, t, J=6Hz), 2.40–2.10(9H, m), 2.05–0.75(10H, m) | 147(100), 314(15), 461(14), 606(3, M⁺) |
| 3 | 7.70–6.85(4H, m), 7.25(5H, s), 5.18(1H, d, J=10Hz), 4.85–3.90(2H, m), 4.20(2H, t, J=6Hz), 3.50(2H, s), 2.65(2H, t, J=6Hz), 2.35–2.10(9H, m), 2.00–0.85(10H, m) | 147(100), 314(31), 424(26), 572(9, M⁺) |
| 4 | 7.45–6.90(4H, m), 7.25(5H, s), 4.73(1H, d, J=10Hz), 4.90–3.90(2H, m), 4.20(2H, t, J=6Hz), 3.52(2H, s), 2.65(2H, t, J=6Hz), 2.40–2.10(9H, m), 2.00–0.85(10H, m) | 147(100), 314(14), 424(8), 572(8, M⁺) |
| 5 | 8.32–7.14(4H, m), 7.30(5H, s), 4.93(1H, d, J=10Hz), 5.08–4.25(2H, m), 4.20(2H, t, J=6Hz), 3.53(2H, s), 2.68(2H, t, J=6Hz), 2.30(6H, broad s), 2.24(3H, s), 1.90–0.91(8H, m) | 134(100), 147(92), 405(12), 552(23), 569(7, M⁺) |
| 6 | 7.66–7.06(4H, m), 7.23(5H, s), 3.40(1H, d, J=12Hz), 4.93–4.15(2H, m), 4.15(2H, t, J=8Hz), 3.50(2H, s), 2.67(2H, t, J=8Hz), 2.40(3H, broad s), 2.22(3H, s), 2.13(3H, s), 1.87–0.80(8H, m) | 134(43), 147(100), 300(20), 447(21), 592(8, M⁺) |
| 7 | 7.45–6.97(4H, m), 7.25(5H, s), 4.75(1H, d, J=11Hz), 4.94–4.13(2H, m), 4.20(2H, t, J=6Hz), 3.53(2H, s), 2.67(2H, t, J=6Hz), 2.24(9H, broad s), 1.87–0.93(8H, m) | 134(92), 147(100), 300(18), 410(10), 558(12, M⁺) |
| 8 | 7.45–6.72(4H, m), 7.16(5H, s), 5.14(1H, d, J=10Hz), 4.85–4.16(2H, m), 4.15(2H, t, J=6Hz), 3.46(2H, s), 2.63(2H, t, J=6Hz), 2.28(6H, broad s), 2.18(3H, s), 1.75–0.72(8H, m) | 134(100), 147(93), 300(26), 410(14), 558(10, M⁺) |
| 9 | 8.23–7.00(14H, m), 4.85(1H, d, J=11Hz), 4.85–4.41(2H, m), 4.32–4.03(3H, m), 2.83–2.04(16H, m), 1.46–0.78(8H, m) | 68(92), 167(100), 683(42), 700(6, M⁺) |
| 10 | 7.67–7.10(14H, m), 5.36(1H, d, J=10Hz), 4.34–3.92(2H, m), 2.76–2.05(16H, m), 1.91–1.52(2H, m), 1.48–0.76(6H, m) | 167(100), 207(40), 278(42), 428(27), 723(25, M⁺) |
| 11 | 7.65–6.92(14H, m), 5.67(1H, d, J=10Hz), 4.35–3.94(3H, m), 2.86–2.15(16H, m), 1.80–0.87(8H, m) | 167(100), 278(14), 689(6, M⁺) |
| 12 | 8.20–7.00(4H, m), 7.27(5H, s), 4.90(1H, d, J=11Hz), 4.90–4.00(3H, m), 4.20(2H, t, J=6Hz), 3.51(2H, s), 2.67(2H, t, J=6Hz), 2.45–2.20(9H, m), 1.90–0.90(5H, m) | 134(100), 286(5), 391(8), 538(11), 555(2, M⁺) |
| 13 | 7.70–7.00(4H, m), 7.24(5H, s), 5.36(1H, d, J=11Hz), 4.90–3.80(3H, m), 4.13(2H, t, J=6Hz), 3.50(2H, s), 2.65(2H, t, J=6Hz), 2.45–2.10(9H, m), 1.90–0.80(5H, m) | 134(67), 147(100), 286(15), 433(13), 578(4, M⁺) |
| 14 | 7.60–7.00(4H, m), 7.27(5H, s), 4.75(1H, d, J=11Hz), 4.90–4.00(3H, m), 4.19(2H, t, J=6Hz), 3.51(2H, s), 2.66(2H, t, J=6Hz), 2.45–2.10(9H, m), 2.00–0.90(5H, m) | 134(100), 286(13), 396(5), 544(5, M⁺) |
| 15 | 7.60–6.80(4H, m), 7.25(5H, s), 5.16(1H, d, J=11Hz), 4.90–3.90(3H, m), 4.19(2H, t, J=6Hz), 3.50(2H, s), 2.65(2H, t, J=6Hz), 2.45–2.10(9H, m) 2.00–0.85(5H, m) | 147(100), 286(31), 396(21), 544(8, M⁺) |
| 16 | 8.2–7.0(4H, m), 7.2(5H, s), 4.85(1H, d, J=10Hz), 4.4–3.1(8H, m), 2.65(2H, t, J=6Hz), 2.4–2.1(9H, m), 1.0(3H, s), 0.95(3H, s) | 134(100), 405(8), 552(16), 569(7, M⁺) |
| 17 | 7.7–7.0(4H, m), 7.20(5H, s), 5.28(1H, d, J=10Hz), 4.5–3.2(8H, m), 2.60(2H, t, J=6Hz), 2.25–2.05(9H, m), 1.0(3H, s), 0.8(3H, s) | 147(100), 300(15), 447(10), 592(5, M⁺) |
| 18 | 7.5–6.8(4H, m), 7.20(5H, s), 4.70(1H, d, J=10Hz), 4.3–3.3(8H, m), 2.65(2H, t, J=6Hz), 2.20(9H, broad s), 0.9(6H, broad s) | 147(100), 300(15), 410(6), 558(6, M⁺) |
| 19 | 8.1–6.9(4H, m), 7.20(5H, s), 5.12(1H, d, J=10Hz), 4.4–3.3(8H, m), 2.63(2H, t, J=6Hz), 2.15(9H, broad s), 1.0(3H, s), 0.88(3H, s) | 147(100), 300(30), 410(22), 558(13, M⁺) |
| 20 | 7.7–7.1(4H, m), 5.30(1H, d, J=10Hz), 5.0–4.0(3H, m), 3.54(3H, s), 2.40–2.20(6H, m), 1.5–0.8(5H, m) | 300(100), 310(30), 443(12, M⁺) |
| 21 | 7.9–7.0(4H, m), 5.32(1H, d, J=10Hz), 5.0–4.2(2H, m), 3.55(3H, s), 2.35(3H, d, J=3Hz), 2.15(3H, s), 2.0–0.7(8H, m) | 246(15), 309(40), 314(100), 4.59(9, M⁺) |
| 22 | 8.0(1H, broad), 7.7–7.0(4H, m) 5.3(1H, d, J=10Hz), 4.3–3.5(4H, m), 3.60(3H, s), 2.15(6H, broad | 228(27), 314(100), 400(4) |

TABLE 2-continued

Compounds of Examples 1 to 22 and their spectral data

| Example Nos. | NMR spectrum δ-value (in CDCl₃) | Mass spectrum m/e (intensity ratio) |
|---|---|---|
| | s), 1.02(3H, s), 0.89(3H, s) | 459(5, M⁺) |

Test 1: Pharmacological activities of 1,4-dihydropyridine-5-phosphonic acid cyclic esters (1) Calcium antagonistic effects 10 mm in situ length of taenia caecum of guinea pig was suspended at a tension of 1 g in a 20 ml organ bath filled with a physiological salt solution (NaCl: 135 mM, KCl: 5 mM etc.).

This solution was bubbled with a gas mixture of 95% $O_2$-5% $CO_2$ and kept at 37° C. Then, the preparation was depolarized by a K⁺ rich solution (NaCl: 40 mM, KCl: 100 mM). After 10-20 minutes equilibration period, 10 mM of $CaCl_2$ was added to the bathing solution. The contraction was produced, and then the test compound applied cumulatively. The relaxation produced was expressed as percentage of the maximum relaxation produced by $10^{-4}$M papaverine, and the concentration of the compound producing 50% relaxation, i.e. $ID_{50}$ (M), was calculated. The values of $pID_{50}$ ($pID_{50}$ = $-\log [ID_{50}]$) are summarized in Table 3.

(2) Antihypertensive effects

After oral administration of the test compound dissolved in a $H_2O$-PEG 400 solvent mixture ($H_2O$:PEG 400 (w/w)=1:3) to the male spontaneously hypertensive rat (SHR), the systolic blood pressure was measured by a tail cuff method. Prior to the measurement, rats were warmed at 50° C. for five minutes. The results are summarized in Table 3.

TABLE 3

Calcium antagonistic effects and antihypertensive effects of 1,4-dihydropyridine-5-phosphonic acid cyclic esters

| | | Antihypertensive effects | |
|---|---|---|---|
| Compounds | $pID_{50}$ | Dose (mg/kg) | Maximum decrease (%) |
| Nicardipine | 9.38 | 20 | 34 |
| Nifedipine | 8.54 | 10 | 26 |
| Diltiazem | 6.56 | 60 | 10 |
| Hydrochloride of Example 1 | 8.15 | 20 | 50 |
| Hydrochloride of Example 2 | 8.23 | 20 | 45 |
| Hydrochloride of Example 3 | 8.40 | 10 | 15 |
| Hydrochloride of Example 4 | 8.31 | 10 | 15 |
| Hydrochloride of Example 5 | 8.61 | 20 | 50 |
| Hydrochloride of Example 6 | 8.35 | 5 | 37 |
| Hydrochloride of Example 7 | 8.26 | 20 | 49 |
| Hydrochloride of Example 8 | 8.55 | 10 | 47 |
| Hydrochloride of Example 9 | 7.53 | 20 | 36 |
| Hydrochloride of Example 10 | 7.24 | 20 | 46 |
| Hydrochloride of Example 11 | 7.61 | 10 | 29 |
| Hydrochloride of Example 12 | 8.59 | 10 | 18 |
| Hydrochloride of Example 13 | 7.91 | 10 | 39 |
| Hydrochloride of Example 14 | 8.52 | 10 | 14 |
| Hydrochloride of Example 15 | 8.49 | 10 | 38 |
| Hydrochloride of Example 16 | 8.45 | 10 | 21 |
| Hydrochloride of Example 17 | 8.37 | 20 | 42 |
| Hydrochloride of Example 18 | 8.35 | 10 | 17 |
| Hydrochloride of Example 19 | 8.29 | 10 | 30 |
| Hydrochloride of Example 20 | 8.69 | 20 | 32 |

TABLE 3-continued

Calcium antagonistic effects and antihypertensive effects of 1,4-dihydropyridine-5-phosphonic acid cyclic esters

| | | Antihypertensive effects | |
|---|---|---|---|
| Compounds | $pID_{50}$ | Dose (mg/kg) | Maximum decrease (%) |
| Hydrochloride of Example 21 | 8.72 | 20 | 35 |

(1) Nicardipine

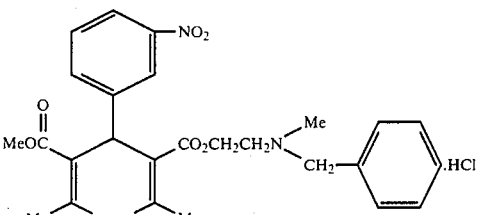

(2) Nifedipine

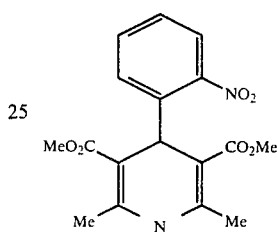

(3) Diltiazem

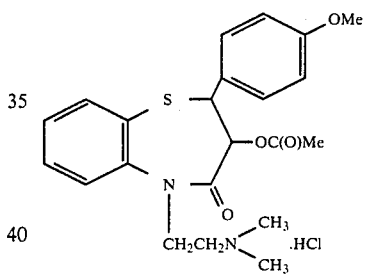

Test 2: Acute toxicity test ddY mice (♂, 4 weeks old) were divided into groups of five mice and the test compound dissolved in purified water was administered orally (5% solution) or intraperitoneally (1% solution) to the male ddY mice.

After seven days, $LD_{50}$ values were calculated from the dead rats recorded in the individual dosage groups by the method of Litchfield-Wilcoxon. The results are shown in Table 4.

TABLE 4

| | $LD_{50}$ (mg/kg) | |
|---|---|---|
| Tested compounds | i.p. | p.o. |
| Nicardipine | 166 | 561 |
| Hydrochloride of the Compound of Example 6 | 17 | 53 |
| Hydrochloride of the Compound of Example 7 | 23 | 74 |

Now, examples will be given for various formulations containing the compound of the formula I.

Tablets

Composition (1,000 tablets):

| | |
|---|---|
| Hydrochloride of the compound of the Example 1 | 5.0 (g) |
| Lactose | 190.0 |
| Corn starch | 75.0 |
| Crystal cellulose powder | 25.0 |
| Methyl cellulose | 3.0 |
| Magnesium stearate | 2.0 |
| | 300.0 |

The above ingredients in the respective amounts were introduced into a twin shell mixer and uniformly mixed. This powder mixture was tableted by a direct compression method to obtain tablets having a weight of 300 mg per tablet.

Capsules

Composition (1,000 capsules):

| | |
|---|---|
| Hydrochloride of the Compound of the Example 1 | 5 (g) |
| Corn starch | 145 |
| Crystal cellulose powder | 145 |
| Magnesium stearate | 5 |
| | 300 |

The above ingredients in the respective amounts were introduced into a twin shell mixer and uniformly mixed. This powder mixture was packed in hard gelatin capsules in an amount of 300 mg per capsule.

Powder

Composition:

| | |
|---|---|
| Hydrochloride of the compound of the Example 1 | 1.0 (g) |
| Lactose | 88.0 |
| Crystal cellulose powder | 10.0 |
| Methyl cellulose | 1.0 |
| | 100.0 |

The above ingredients in the respective amounts were introduced into a twin shell mixer and uniformly mixed to obtain a powder.

Syrups

Composition (2% syrups):

| | |
|---|---|
| Hydrochloride of the compound of the Example 1 | 2.0 (g) |
| Sugar | 30.0 |
| Glycerin | 5.0 |
| Flavoring agent | 0.1 |
| 96% ethanol | 10.0 |
| Methyl p-hydroxybenzoate | 0.03 |
| Purified water to make | 100.0 g |

The sugar and the hydrochloride of the compound of Example 1 were dissolved in 60 g of warm water, and after cooling the solution, a solution of the flavoring agent in glycerin and ethanol was added. Then, water was added to this mixture to bring the total amount to 100.0 g.

We claim:

1. A compound of the formula:

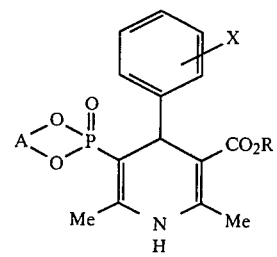

wherein
X is hydrogen, nitro, trifluoromethyl, fluorine, chlorine, bromine, or iodine;
A is 1,3-propylene or 1,4-butylene which may be substituted by $C_1$–$C_3$ alkyl;
R is $C_1$–$C_4$ alkyl, —Y—N($R^1$)($R^2$) or

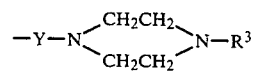

wherein each of $R^1$, $R^2$ and $R^3$, which may be the same or different, and is hydrogen, $C_1$–$C_6$ alkyl, or aralkyl; and Y is $C_2$–$C_6$ alkylene; and
Me is methyl; or its pharmaceutically acceptable salt.

2. The compound of claim 1, wherein
A is 1,3-propylene or 1,4-butylene which may be substituted by one or two methyl groups, and
R is

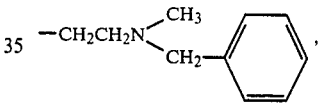

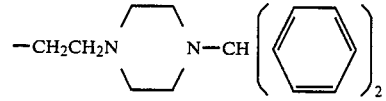

or $C_1$–$C_4$ alkyl.

3. The compound of claim 1, wherein
A is

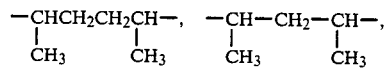

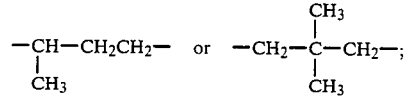

R is

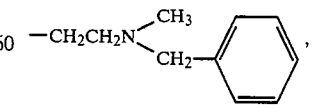

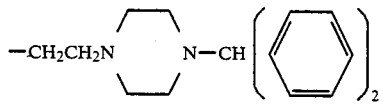

or CH₃; and

X is NO₂, CF₃, F, Cl, Br or I substituted at the 2- or 3-position.

4. The compound of claim 3, wherein R is

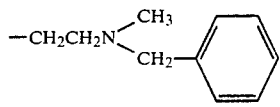

5. The compound of claim 4, wherein X is CF₃, NO₂ or Cl substituted at the 2- or 3-position.

6. An antihypertensive, coronary or peripheral vasodilator composition comprising (a) an antihypertensive, coronary or peripheral vasodilator effective amount of the compound of claim 1; and (b) a pharmaceutically acceptable diluent or carrier.

7. A method of treating hypertension in a subject in need of such treatment comprising administering to the subject an antihypertensive effective amount of the compound of the formula I as defined in claim 1 to produce such effect.

8. A method of producing coronary vasodilation in a patient in need of such treatment comprising administering to the patient a coronary vasodilating effective amount of the compound of claim 1 to produce such effect.

9. A method of producing peripheral vasodilation in a patient in need of such treatment comprising administering to the patient a peripheral vasodilating effective amount of the compound of claim 1 to produce such effect.

* * * * *

Notice of Adverse Decision in Interference

In Interference No. 101,734, involving Patent No. 4,576,934, K. Seto, S. Tanaka, R. Sakoda, ANTIHYPERTENSIVE DIHYDROPYRIDINE-5-PHOSPHONIC ACID CYCLIC ESTERS, final judgement adverse to the patentees was rendered Oct. 12, 1990, as to claims 1-11.
*(Official Gazette March 5, 1991)*